United States Patent [19]

Hasler et al.

[11] Patent Number: 4,587,256

[45] Date of Patent: May 6, 1986

[54] NOVEL THIAZOLIDINE DERIVATIVES

[75] Inventors: Heinz Hasler, Kaiseraugst; Fernand Schneider, Basel, both of Switzerland

[73] Assignee: Hoffmann-La Roche Inc., Nutley, N.J.

[21] Appl. No.: 619,655

[22] Filed: Jun. 11, 1984

[30] Foreign Application Priority Data

Jun. 23, 1983 [CH] Switzerland .......................... 3432/83
Apr. 13, 1984 [CH] Switzerland .......................... 1860/84

[51] Int. Cl.[4] .................. C07D 513/10; C07D 277/60; A61K 31/425
[52] U.S. Cl. ...................................... 514/369; 548/147
[58] Field of Search .......................... 548/147; 514/369

[56] References Cited

PUBLICATIONS

Sohda et al., Chem. Pharm. Bull. 30 3601 (1983).

*Primary Examiner*—Robert Gerstl
*Attorney, Agent, or Firm*—Jon S. Saxe; Bernard S. Leon; William G. Isgro

[57] ABSTRACT

The invention relates to with novel thiazolidine derivatives of the formula

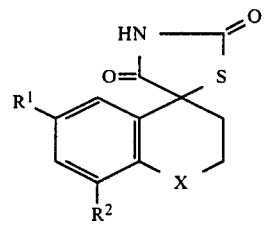

wherein X is methylene, oxygen or sulfur; $R^1$ is halogen; $R^2$ is hydrogen, nitro, cyano, $OR^3$ or $NHR^3$; or $R^1$ and $R^2$ both simultaneously are hydrogen or nitro; $R^3$ is hydrogen, alkyl, acyl, —CO—$OR^4$ or —CO—$NHR^4$; and $R^4$ is alkyl, unsubstituted or substituted aryl or aralkyl, and their salts with physiologically compatible cations. The compounds of formula I are useful in the treatment of metabolic disorders.

22 Claims, No Drawings

NOVEL THIAZOLIDINE DERIVATIVES

BRIEF SUMMARY OF THE INVENTION

The invention relates to thiazolidine derivatives of the formula

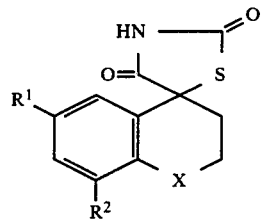

wherein

X is methylene, oxygen or sulfur; $R^1$ is halogen; $R^2$ is hydrogen, nitro, cyano, $OR^3$ or $NHR^3$; or $R^1$ and $R^2$ both simultaneously are hydrogen or nitro; $R^3$ is hydrogen, alkyl, acyl, —CO—$OR^4$ or —CO—$NHR^4$; and $R^4$ is alkyl, unsubstituted or substituted aryl or aralkyl;

and their salts with physiologically compatible cations. The compounds of formula I are useful in the treatment of diabetes mellitus.

The invention relates to a process for the preparation of the compounds of formula I and of salts thereof, pharmaceutical preparations containing the compounds of formula I as well as their use as medicaments, especially in the treatment of metabolic illnesses.

DETAILED DESCRIPTION OF THE INVENTION

The invention relates to thiazolidine derivatives of the formula

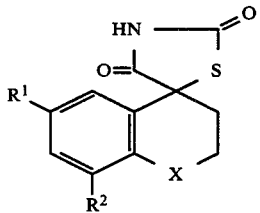

wherein

X is methylene, oxygen or sulfur; $R^1$ is halogen; $R^2$ is hydrogen, nitro, cyano, $OR^3$ or $NHR^3$; or $R^1$ and $R^2$ both simultaneously are hydrogen or nitro; $R^3$ is hydrogen, alkyl, acyl, —CO—$OR^4$ or —CO—$NHR^4$; and $R^4$ is alkyl, unsubstituted or substituted aryl or aralkyl, and their salts with physiologically compatible cations.

As used herein, halogen denotes chlorine, fluorine, bromine and iodine, the preferred substituents are fluorine and chlorine. Alkyl groups can be straight-chain or branched-chain and preferably containing 1–12 carbon atoms. Examples of such groups are methyl, ethyl, propyl, butyl, pentyl, hexyl, decyl, dodecyl and the like. Acyl denotes, preferably, alkanoyl containing 1–12 carbon atoms and aroyl containing 7 to 14 carbon atoms, such aryl groups can be derived from carboxylic acids, for example, aliphatic, aromatic or araliphatic carboxylic acids which preferably contain 1–12 carbon atoms such as acetic acid, propionic acid, butyric acid, caproic acid, undecanoic acid, dodecanoic acid, aceto- acetic acid, acetylglycolic acid, benzoic acid, substituted benzoic acids such as p-toluic acid, p-nitrobenzoic acid, p-chlorobenzoic acid, p-bromobenzoic acid and m-dinitrobenzoic acid; naphthoic acid, phenylacetic acid; or aliphatic or aromatic sulfonic acids such as methanesulfonic acid, ethanesulfonic acid, benzenesulfonic acid or p-toluenesulfonic acid. Alkyl groups denoted by $R^4$ preferably contain 1–6 carbon atoms, examples, methyl, ethyl, propyl, isopropyl, butyl and isobutyl. Examples of aryl groups are phenyl and substituted phenyl groups such as halophenyl, nitrophenyl and alkoxycarbonylphenyl. Examples of aralkyl group are $C_{1-6}$-alkyl groups which are substituted by one of the aforementioned aryl groups, for example, benzyl and nitrobenzyl. Examples of physiologically compatible cations are alkali metal and alkaline earth metal ions, such as, $Na^+$, $K^+$, $Ca^{++}$, $Mg^{++}$ and the like.

The compounds of formula I wherein X is methylene, oxygen or sulfur; $R^1$ is halogen; $R^2$ is hydrogen, nitro, cyano or $NHR^3$; and $R^3$ is hydrogen, alkyl or acyl, are of particular interest.

Preferred compounds of formula I are those in which X is oxygen; further preferred are those in which $R^1$ is halogen, especially fluorine. 6-Fluoro-8-acetamido-2,3-dihydrospiro[4H-1-benzopyran-4,5'-thiazolidine]-2',4'-dione and ($\pm$)-methyl-6-fluoro-2,3-dihydro-2',4'-dioxospiro[4H-1-benzopyran-4,5'-thiazolidine]-8-carbamate are of particular interest.

The compounds of formula I and their salts can be obtained as racemates and in optically active form. Optically active compounds of formula I can be obtained from the racemates in a known manner by racemate resolution, for example, by chromatography on an optically active carrier or by reaction with optically active bases, such as brucine, separation of the diastereomeric salts by fractional crystallization and conversion of the salt into the free acid, that is, the optically active compound of formula I. They can also be obtained by using an optically active compound of formula II as the starting material. The optically active compound of formula II can be obtained, in turn, by racemate resolution.

The compounds of formula I can be prepared in accordance with the invention by treating a compound of the formula

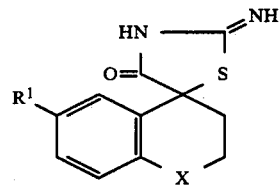

wherein $R^1$ and X are as previously described, with an acid, if desired, nitrating the reaction product, if desired, reducing the nitro group in a thus-obtained compound of formula I in which $R^1$ is halogen to the amino group and, if desired, acylating or alkylating the amino group or replacing said group by the cyano or hydroxy group; if desired, alkylating or acylating the hydroxy group; and if desired, converting the reaction product into a salt with a physiologically compatible cation.

The hydrolysis of the imino group in a compound of formula II can be carried out by treatment with strong acids for example, mineral acids, such as aqueous-alcoholic hydrochloric acid, preferably while heating up to the reflux temperature of the reaction mixture. A thus-obtained compound of formula I in which $R^1$ is halogen or hydrogen and $R^2$ is hydrogen can be nitrated to give a compound of formula I in which $R^2$ is a nitro group or $R^1$ and $R^2$ both are a nitro group. This nitration can be carried out in a known manner for the nitration of aromatic compounds, for example, by treatment with a nitrating agent such as strong nitric acid at temperatures in the range of about −20° C. to about room temperature. A compound of formula I wherein $R^1$ is halogen and $R^2$ is nitro can be reduced in a known manner for the reduction of aromatic nitro compounds. Suitable reducing agents are, for example, hydrogen in the presence of catalysts, especially noble metal catalysts, such as, platinum oxide or palladium catalysts; or nascent hydrogen, for example iron/HCl, Raney-nickel; or ammonium sulfide in aqueous alcohol.

The amino group $R^2$ in a thus-obtained compound of formula I can be alkylated or acylated in a known manner by treatment with an alkylating agent or an acylating agent. Suitable alkylating agents are alkyl halides, such as, methyl iodide or ethyl iodide in the presence of a base, such as, potassium carbonate or pyridine in an inert solvent, for example, ethanol. Examples of acylating agents are reactive acid derivatives, such as, acid anhydrides, acid halides, activated esters, for example, nitrophenyl esters. The replacement of the amino group by the cyano or hydroxy group can be carried out in a known manner by diazotization and reaction of the diazonium salt with copper (I) cyanide or, for the purpose of introducing the hydroxy group, with copper salts such as copper (II) nitrate by copper (I) catalysis. The acyl groups —$COOR^4$ and —$CONHR^4$ can be introduced by reacting a compound of formula I in which $R^2$ is an amino or hydroxy group with an isocyanate of the formula $R^4NCO$ or a chloroformic acid ester of the formula $R^4OCOCl$.

The compounds of formula II also form part of the invention, and can be prepared as illustrated in Formula Scheme I.

Formula Scheme I

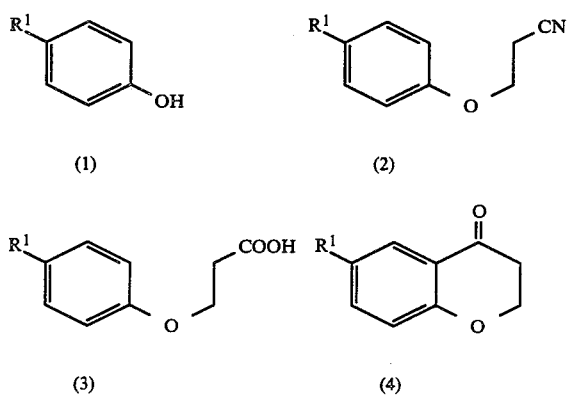

-continued
Formula Scheme I

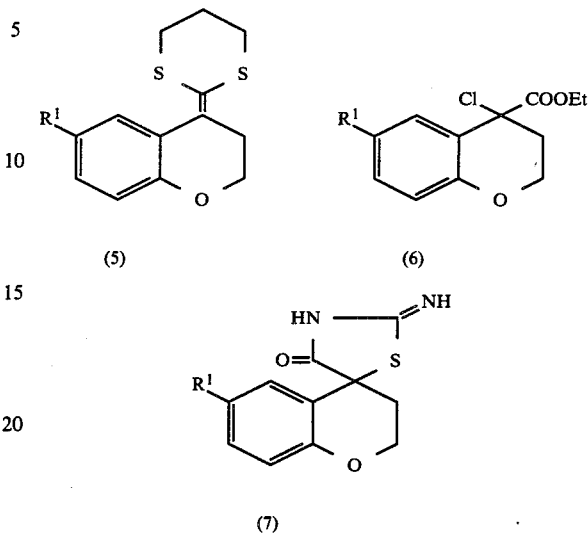

A compound (1) can be converted into the compound (2) by treatment with acrylonitrile in the presence of a base, such as, sodium methylate while heating to reflux temperature. Hydrolysis of the nitrile (2) by heating to reflux with strong aqueous hydrochloric acid yields the compound (3) from which (4) is obtained by treatment with hot polyphosphoric acid. The synthesis of the thiazolidine group proceeds stepwise via a Peterson olefination with 2-lithio-2-trimethylsilyl-1,3dithiane to yield the compound (5). Oxidation with N-chlorosuccinimide in the presence of an alcohol, preferably ethanol, yields the not very stable α-chloroester (6). This is boiled for a long time in the presence of thiourea in an inert solvent, such as, acetone, whereby the chlorine atom is replaced by the thiourea group and spontaneous cyclization to the spiro-imino compound (7) takes place. The product precipitates as the hydrochloride and the free base is isolated after chromatography on silica gel. The compounds of formula II in which X is sulfur can be prepared in an analogous manner starting from thiophenols corresponding to the phenols (1) and the compounds of formula II in which X is methylene can be prepared in an analogous manner starting from tetralones corresponding to the chromanones (4).

The compounds of formula I and their salts are physiologically active, particularly, as aldose reductase inhibitors.

In the testing for their inhibiting activity of aldose reductase from calves lenses [J. Biol. Chem. 240, 877 (1965), the compounds of formula I in which $R^1$ is fluorine and $R^2$ is hydrogen, nitro or acetamido produced $IC_{50}$ values (concentrations which bring about 50% enzyme inhibition) of 0.10μM, 0.089μM and 0.008μM, respectively.

Furthermore, the compound of formula I in which $R^1$ is fluorine and $R^2$ is hydrogen was investigated for its activity on galactosaemic rats (30% galactose diet). More particularly, the dulcitol concentration in the eye lens was determined after 5 applications of 5 and of 20 mg/kg body weight per os over 2 days. Similarly, 20 mg/kg were administered intraperitoneally in an additional experiment. In all experiments, a significant decrease in the dulcitol concentration in the eye lens was established by comparison to untreated galactosaemic animals. The same compound was also administered to streptozotocin-treated, diabetic rats (3 times 20 mg/kg p.o., 4, 8 and 24 hours after streptozotocin administration). Three (3) hours after the administration of the last dosage, the sorbitol concentration was determined in the eye lens and in the sciatic nerve. In both organs a clear decrease in the sorbitol concentration was detected as compared to treated, diabetic animals.

The compounds of formula I and their physiologically compatible salts can be used as active substances in pharmaceutical preparations. More particularly, they can be used for the treatment of diabetes mellitus and for the prevention of complications, such as, cataract and neuropathies which appear due to such disease condition. The compounds can be administered orally or parenterally in dosages of 0.1–5 mg/kg body weight giving due consideration to the mode of administration and the requirements of the patient. The pharmaceutical preparations can be administered, for example, in the form of tablets, dragées, capsules, infusion solutions, eye drops or eye ointments, which besides the active substance can contain adjuvants and carrier materials which are conventional in such preparations. The pharmaceutical preparations can be prepared using known galenical techniques.

The Examples which follow further illustrate the invention:

EXAMPLE 1

2.195 g of (±)-6-fluoro-2,3-dihydro-2′-iminospiro-[4H-1-benzopyran-4,5′-thiazolidin]-4′-one were dissolved in 12 ml of methanol and 12 ml of 37% aqueous hydrochloric acid and the solution was boiled overnight. The colorless crystals which separated were removed and washed with water. After drying in vacuo, there was obtained (±)-6-fluoro-2,3-dihydrospiro[4H-1-benzopyran-4,5′-thiazolidine]-2′,4′-dione of melting point 147°–149° C. (95% of theory).

The starting material was prepared as follows:

5.4 g of sodium methylate were added portionwise at 60° C. to 112.1 g of 4-fluoro-phenol. After 10 minutes, the mixture was treated with 500 ml of acrylonitrile, boiled in an oil-bath for 48 hours, thereafter poured into 3 l of water and extracted with chloroform. After drying the organic phase with sodium sulfate, it was concentrated completely in vacuo. There was obtained 3-(4-fluoro-phenoxy)propionitrile as a viscous oil.

155 g of 3-(4-fluoro-phenoxy)propionitrile were introduced into 5 l of hot 25% aqueous hydrochloric acid and the mixture was boiled for 2 hours. The solution was left to stand overnight, whereby the 3-(4-fluoro-phenoxy)propionic acid crystallized in the form of colorless needles of melting point 84°–85° C.

135 g of 3-(4-fluoro-phenoxy)propionic acid were introduced portionwise into 1.5 kg of polyphosphoric acid at 100° C. with vigorous stirring and the temperature rose to 116° C. After 30 minutes, the mixture was poured on to 6 l of ice-water and extracted with four portions of chloroform. The extract was dried with sodium sulfate and concentrated completely. The residue was dissolved in ethanol and boiled with 10 g of active carbon. The filtered solution was concentrated while hot up to saturation and then left to stand, whereby 81 g of 6-fluoro-4-chromanone of melting point 110°–112° C. crystallized. A sample of the brown-red product was sublimed at 100° C. in a high vacuum and yielded colorless crystals of melting point 113°–114° C.

28.8 g of 2-trimethylsilyl-1,3-dithiane were dissolved in 290 ml of peroxide-free tetrahydrofuran and the solution was treated dropwise at −60° C. with 93 ml of a 1.6M solution of n-butyl lithium in hexane. The mixture was left to warm to 0° C. within 3 hours and subsequently again cooled to −60° C. A solution of 24.87 g of 6-fluoro-4-chromanone in 150 ml of tetrahydrofuran was subsequently slowly added dropwise and the mixture was left to warm slowly from −60° C. to room temperature while stirring overnight. The mixture was subsequently poured into 2.5 l of water and extracted with four portions of ethyl acetate. The organic extracts were washed with saturated sodium chloride solution and dried with sodium sulfate The concentrated extract was decolorized with active carbon in a mixture of ether and low-boiling petroleum ether (1:1) and crystallized from the same mixture in the cold. After two recrystallizations, the combined mother liquors were chromatographed on a silica gel 60 column [hexane/ethyl acetate (9:1)]. The product-containing fractions were concentrated and the residue was recrystallized. There was obtained 4-m-dithian-2-ylidene-6-fluoro-2,3-dihydro-4H-1-benzopyran of melting point 47°–49° C.

A solution of 10.73 g of 4-m-dithian-2-ylidene-6-fluoro-2,3-dihydro-4H-1-benzopyran in 107 ml of tetrahydrofuran was slowly added dropwise at room temperature to 26.7 g of freshly crystallized N-chlorosuccinimide dissolved in 210 ml of acetonitrile and 105 ml of ethanol. The mixture was stirred at room temperature for 3 hours, subsequently hydrolyzed by the addition of 100 ml of water, diluted with 1 l of water and extracted with three portions of ethyl acetate. The organic phases were washed twice with water and once with saturated sodium chloride solution, dried with sodium sulfate and concentrated to dryness in vacuo. Excess N-chlorosuccinimide and resulting succinimide were separated by filtration through a layer of silica gel 60 with hexane/ethyl acetate (19:1). The thus-obtained crude α-chloro-ethyl ester was dissolved in 85 ml of acetone, the solution was treated with 2.48 g of thiourea and the mixture was dried for 4 days. The initially clear solution liberated colorless crystals. These were separated, washed with acetone and recrystallized from ethanol/ethyl acetate, and there was obtained (±)-6-fluoro-2,3-dihydro-2′-iminospiro[4H-1-benzopyran-4,5′-thiazolidin]-4′-one hydrochloride of melting point 215°–217° C.

The filtrate was concentrated and the residue was chromatographed on 500 g of silica gel 60 [chloroform/methanol (9:1)]. A first fraction ($R_f$=0.82) contained unreacted starting material together with its decomposition products. The free base of melting point 255°–258° C. was isolated from the main fraction ($R_f$=0.31) by crystallization from ethanol/ethyl acetate. A sample of this material was sublimed at 200°–210° C./$10^{-2}$ mbar and melted at 261°–263° C.

EXAMPLE 2

Into 2.5 ml of fuming nitric acid (96%, d 1.50), which had been cooled to −20° C. while stirring, there was introduced rapidly 500 mg of (±)-6-fluoro-2,3-dihydrospiro[4H-1-benzopyran-4,5′-thiazolidine]-2′,4′-dione so that the temperature did not exceed −15° C. After stirring at −20° C. for 3 minutes, there was obtained a clear solution which was then poured immediately on to 15 ml of ice-water. After stirring briefly, the resulting precipitate was filtered, washed with cold water and dried. There was obtained (±)-6-fluoro-8-nitro-2,3-dihydrospiro[4H-1-benzopyran-4,5'-thiazolidine]-2',4'-dione in the form of yellow crystals which melted at 192°–194° C. after recrystallization from ethyl acetate/hexane.

EXAMPLE 3

(a) 755 mg of (±)-6-fluoro-8-nitro-2,3-dihydrospiro[4H-1-benzopyran-4,5'-thiazolidine]-2',4'-dione were hydrogenated at room temperature and normal pressure in the presence of 50 mg of platinum oxide in 50 ml of ethanol. An additional 100 mg of platinum oxide were added after 30 minutes. After 2.5 hours under hydrogen, some chloroform was added, the catalyst was filtered, the filtrate was concentrated and the residue was chromatographed on silica gel 60 with chloroform/methanol (19:1). (±)-6-Fluoro-8-amino-2,3-dihydrospiro[4H-1-benzopyran-4,5'-thiazolidine]-2',4'-dione was obtained in the form of a yellowish foam. The IR spectrum showed amine bands at 3383, 3202 and 2766 cm$^{-1}$, in the mass spectrum the molecular ion appeared as a basic peak (m/e=268).

(b) 100 mg of (±)-6-fluoro-8-nitro-2,3-dihydrospiro[4H-1-benzopyran-4,5'-thiazolidine]-2',4'-dione were taken up in 500 μl of ethanol and 250 μl of water together with 57 mg of iron powder. After the addition of 250 μl of 0.16N hydrochloric acid, the mixture was held at 100° C. on an oil-bath for 2 hours. The mixture was subsequently filtered, the filtrate was extracted with three portions of ethyl acetate, the extracts were dried with sodium sulfate and, after concentration, the residue was chromatographed on silica gel [ethyl acetate/ethanol (9:1)]. The product was identical with that obtained in paragraph (a).

(c) 12 g of (±)-6-fluoro-8-nitro-2,3-dihydrospiro[4H-1-benzopyran-4,5'-thiazolidine-]2',4'-dione were taken up in 250 ml of ethanol and brought into solution by the addition of 25 ml of 25% aqueous ammonia. A solution of 60 g of sodium sulfide and 13.37 g of ammonium chloride in 250 ml of water was poured into the solution obtained and the mixture was boiled for 3 hours. The mixture was poured into 2 l of cold water and acidified to pH 5–5.5 by the addition of 25% hydrochloric acid. The product was extracted with three portions of ethyl acetate, the organic phases were washed with saturated sodium chloride solution and dried with sodium sulfate. After removing the solvent, the residue was recrystallized from chloroform and yielded beige crystals of melting point 179°–181° C. The product corresponding in all spectroscopic data to the products described in paragraphs (a) and (b).

EXAMPLE 4

61 mg of (±)-6-fluoro-8-amino-2,3-dihydrospiro[4H-1-benzopyran-4,5'-thiazolidine]-2',4'-dione were heated to 50° C. for 90 minutes in a mixture of 1.2 ml of glacial acetic acid and 1.2 ml of acetic acid anhydride and the resulting mixture was subsequently concentrated to dryness in vacuo. After boiling up briefly with active carbon in methanolic solution, the residue was crystallized from methanol and yielded (±)-6-fluoro-8-acetamido-2,3-dihydrospiro[4H-1-benzopyran-4,5'-thiazolidine]-2',4'-dione in the form of a light brownish material of melting point 278°–280° C.

EXAMPLE 5

In analogy to Example 4, from (±)-6-fluoro-8-amino-2,3-dihydrospiro[4H-1-benzopyran-4,5'-thiazolidine]-2',4'-dione and the mixed anhydride from acetic acid and formic acid in formic acid there was obtained (±)-N-[6-fluoro-2,3-dihydro-b 2',4'-dioxospiro[4H-1-benzopyran-4,5'-thiazolidine]8-yl]formamide of melting point 144°–146° C.

EXAMPLE 6

In analogy to Example 1, (±)-6-chloro-2,3-dihydrospiro[4H-1-benzopyran-4,5'-thiazolidine]2',4'-dione of melting point 161°–163° C. was obtained from (±)-6-chloro-2,3-dihydro-2'-iminospiro[4H-1-benzopyran-4,5'-thiazolidine]4'-one. The starting material was prepared from 6-chloro-4-chromanone via 4-m-dithian-2-ylidene-6-chloro-2,3-dihydro-4H-1-benzopyran, melting point 87°–89° C.

EXAMPLE 7

161 mg of (±)-6-fluoro-8-amino-2,3-dihydrospiro[4H-1-benzopyran-4,5'-thiazolidine]-2',4'-dione were dissolved in 3.5 ml of pyridine and esterified with 135 mg of undecanoyl chloride. After stirring at room temperature for 6 hours, the majority of the pyridine was removed in vacuo, the residue was extracted with three portions of ethyl acetate and two portions of 1N hydrochloric acid, the organic phases were washed neutral with water and with saturated sodium chloride solution, dried with sodium sulfate and concentrated. The residue was chromatographed on silica gel with chloroform/methanol (19:1). With R$_f$=0.27 there were eluted 182 mg of material in the form of a resin which yielded, from methanol, (±)-6-fluoro-8-undecylamido-2,3-dihydrospiro[4H-1-benzopyran-4,5'-thiazolidine]-2',4'-dione in the form of colorless crystals of melting point 69°–71° C.

EXAMPLE 8

The following compounds were prepared in analogy to Example 7:

(±)-N-[6-fluoro-2,3-dihydro-2',4'-dioxospiro[4H-1-benzopyran-4,5'-thiazolidin]-8-yl-pivalamide, amorphous solid, MS: m/e=352: M+1, 61%; m/e=57: 100%;

(±)-N-[6-fluoro-2,3-dihydro-2',4'-dioxospiro[4H-1-benzopyran-4,5'-thiazolidin-8-yl]-3,3-dimethylbutyramide, amorphous solid, MS: m/e=366: M+, 30%, m/e=268:100%; m/e=57: 79%;

(±)-N-[6-fluoro-2,3-dihydro-2',4'-dioxospiro[4H-1-benzopyran-4,5'-thiazolidin]-8-yl]benzamide, melting point 270°–272° C.

(±)-p-bromo-N-2,3-dihydro-6-fluoro-2',4'-dioxospiro[4H-1-benzopyran-4,5'-thiazolidin-8-yl]-benzamide, melting point 297°–298° C.;

(±)-N-[6-fluoro-2,3-dihydro-2',4'-dioxospiro[4H-1-benzopyran-4,5'-thiazolidin-8-yl]-p-nitrobenzamide, melting point above 300° C. MS: m/e=417: 47%; m/e=150: 100%;

(±)-N-[6-fluoro-2,3-dihydro-2',4'-dioxospiro[4H-1-benzopyran-4,5'-thiazolidin[-8-yl]-3,5-dinitrobenzamide, melting point 220°–224° C.

(±)-[[6-fluoro-2,3-dihydro-2',4'-dioxospiro[4H-1-benzopyran-4,5'-thiazolidin]-8-yl]carbamoyl]methylacetate, melting point 221°–223° C.

EXAMPLE 9

210 μl of ethyl chloroformate were added dropwise to a solution of 536 mg of (±)-6-fluoro-8-amino-2,3-dihydrospiro[4H-1-benzopyran-4,5'-thiazolidine]-2',4'-dione in 5.3 ml of pyridine. The mixture was stirred at room temperature overnight. The majority of the pyridine was removed in vacuo and the residue was taken up in ethyl acetate and washed with 0.2N hydrochloric acid and saturated sodium chloride solution. The combined organic phases were dried with sodium sulfate and subsequently concentrated. After purification of the residue by chromatography on a silica gel column using chloroform/ethyl acetate (9:1) for the elution, the (±)-ethyl-6-fluoro-2,3-dihydro-2',4'-dioxospiro[4H-1-benzopyran-4,5'-thiazolidine]-8-carbamate was recrystallized from ethyl acetate/n-hexane and yielded colorless crystals of melting point 170°–172° C.

EXAMPLE 10

The following compounds were prepared in analogy to Example 9:

(±)-Methyl-6-fluoro-2,3-dihydro-2',4'-dioxospiro[4H-1-benzopyran-4,5'-thiazolidine]-8-carbamate, melting point 128°–130° C.;

(±)-t-butyl-6-fluoro-2,3-dihydro-2',4'-dioxospiro[4H-1-benzopyran-4,5'-thiazolidine]-8-carbamate, melting point 132°–134° C.;

(±)-isobutyl-6-fluoro-2,3-dihydro-2',4'-dioxospiro[4H-1-benzopyran-4,5'-thiazolidine]-8-carbamate, melting point 166°–168° C.;

(±)-phenyl-6-fluoro-2,3-dihydro-2',4'-dioxospiro[4H-1-benzopyran-4,5'-thiazolidine]-8-carbamate, melting point 198°–200° C.;

(±)-benzyl-6-fluoro-2,3-dihydro-2',4'-dioxospiro[4H-1-benzopyran-4,5'-thiazolidine]-8-carbamate, melting point 214°–216° C.;

(±)-p-nitrophenyl-6-fluoro-2,3-dihydro-2',4'-dioxospiro[4H-1-benzopyran-4,5'-thiazolidine]-8-carbamate, melting point 160°–162° C.;

(±)-p-nitrophenyl-6-fluoro-2,3-dihydro-2',4'-dioxospiro[4H-1-benzopyran-4,5'-thiazolidine]-8-carbamate, melting point 175°–177° C.;

(±)-p-(methoxycarbonyl)phenyl-6-fluoro-2,3-dihydro-2',4'-dioxospiro[4H-1-benzopyran-4,5'-thiazolidine]-8-carbamate, melting point 159°–161° C.

EXAMPLE 11

268 mg of (±)-8-amino-6-fluoro-2,3-dihydrospiro[4H-1-benzopyran-4,5'-thiazolidine]-2',4'-dione were stirred in 2 ml of tetrahydrofuran with 100 μl of ethyl isocyanate at room temperature for 2.5 hours and the mixture was subsequently heated to 50° C. for an additional 2 hours. The liquid constituents were removed under reduced pressure, he residue was purified by chromatography on a silica gel column using hexane/ethyl acetate (1:2) for the elution, decolorized with active carbon and recrystallized from ethyl acetate/hexane. (±)-1-Ethyl-3-[6-fluoro-2,3-dihydro-2',4'-dioxospiro[4H-1-benzopyran-4,5'-thiazolidin]-8-yl]-urea was obtained in the form of colorless crystals of melting point 197°–199° C.

EXAMPLE 12

5.144 g of (±)-8-amino-6-fluoro-2,3-dihydrospiro[4H-1-benzopyran-4,5'-thiazolidine]-2',4'-dione were introduced into 50 ml of 25% aqueous hydrochloric acid and the mixture was treated dropwise in an ice-bath with a solution of 1.45 g of sodium nitrite in 6 ml of water. After stirring at 0° C. for 60 minutes, the excess nitrite was destroyed by the addition of a spatula tip of urea.

In a separate operation, a solution of 20.59 g of potassium cyanide in 100 ml of water was treated at 0° C. in small portions with 8.58 g of copper (I) cyanide. 35.6 g of sodium bicarbonate were subsequently introduced and the solution was covered with ethyl acetate.

The solution of the diazonium salt prepared above was now poured into this copper cyanide solution and the mixture, from which nitrogen evolved with vigorous foaming, was stirred at room temperature for 0.5 hour. The mixture was subsequently acidified to pH 5.5 by the cautious addition of 25% hydrochloric acid and the product was extracted by shaking-out with three portions of ethyl acetate. The organic phases were back-washed with saturated sodium chloride solution and dried with sodium sulfate. After removing the solvent by concentration, the residue was purified by chromatography on silica gel using chloroform/ethyl acetate (4:1) for the elution and subsequently recrystallized from a mixture of ethyl acetate and n-hexane. (±)-8-Cyano-6-fluoro-2,3-dihydrospiro[4H-1-benzopyran-4,5'-thiazolidine]-2',4'-dione was obtained in the form of yellowish crystals of melting point 230°–232° C.

EXAMPLE 13

268 mg of (±)-8-amino-6-fluoro-2,3-dihydrospiro[4H-1-benzopyran-4,5'-thiazolidine]-2',4'-dione were introduced into 3 ml of 50% tetrafluoroboric acid and the mixture was treated dropwise in an ice-bath with a solution of 76 mg of sodium nitrite in 0.3 ml of water. The mixture was subsequently stirred at room temperature for 90 minutes and then excess nitrite was destroyed by the addition of some urea. The solution of the diazonium salt was introduced in one portion into a solution of 12.08 g of copper (II) nitrate in 25 ml of water with vigorous stirring. After the addition of a small spatula tip of copper (I) oxide, vigorous gas evolution occurred. The mixture was stirred at room temperature until the foaming had finished (about 90 minutes). The product was thereupon extracted with three portions of ether, the organic phases were washed four times with water and dried with sodium sulfate. The residue remaining after removal of the solvent by concentration was separated by chromatography on preparative thick-layer plates and the (±)-6-fluoro-8-hydroxy-2,3-dihydrospiro[4H-1-benzopyran-4,5'-thiazolidine]-2',4'-dione was isolated as a non-crystallizable, solid material.

EXAMPLE 14

2.00 g of (±)-6-fluoro-2,3-dihydrospiro[4H-1-benzopyran-4,5'-thiazolidine]-2',4'-dione and 3.116 g of brucine were heated to boiling in 60 ml of ethanol, whereby spontaneous crystallization occurred after about 10 minutes. The mixture was left to cool to room temperature after 15 minutes. The crystals were separated on a suction filter and, after drying, yielded 2.538 g of material of melting point 146°–148° C., $[\alpha]_D^{25} = 38.5°$ (c=1 in chloroform). These crystals were taken up in 50 ml of ethyl acetate and stirred vigorously with 25 ml of 1N hydrochloric acid for 15 minutes. The ethyl acetate phase was separated and backextracted with an additional 25 ml of hydrochloric acid and with 25 ml of saturated sodium chloride solution. After drying with sodium sulfate the ethyl acetate phase was concentrated and the residue was purified by chromatography on a silica gel column using hexane/ether (1:1) for the elution. There were obtained 948 mg of colorless amorphous material which could not be crystallized; $[\alpha]_D^{25} = +140.2°$ (c=1 in methanol), the $^1$H-NMR spectrum was identical with that of the racemic material. The mother liquor of the brucine salt was concentrated and gave 3.005 g of non-crystallizable foam from which the free acid was liberated in the same manner as for the crystalline material and from which there were obtained 938 mg of amorphous material; $[\alpha]_D^{20} = -139.4°$ (c=1 in methanol).

EXAMPLE A

A tablet having the following composition can be prepared:

| | |
|---|---|
| A compound of formula I | 1–10 parts by weight |
| Sodium citrate | 5 parts by weight |
| Alginic acid | 2 parts by weight |
| Polyvinylpyrrolidone | 2 parts by weight |
| Magnesium stearate | 1 part by weight |

The ingredients are mixed and pressed into tablets which contain 20–200 mg of active substance.

We claim:

1. A compound of the formula

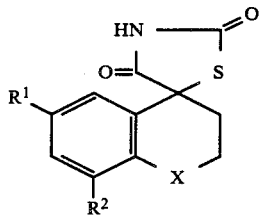

wherein

X is methylene, oxygen or sulfur $R^1$ is halogen; $R^2$ is hydrogen nitro, cyano, $OR^3$ or $NHR^3$; or $R^1$ and $R^2$ both simultaneously are hydrogen or nitro; $R^3$ is hydrogen, alkyl of 1 to 12 carbon atoms, alkanoyl of 1 to 12 carbon atoms, aroyl of 7 to 14 carbon atoms, —CO—$OR^4$ or —CO—$NHR^4$; and $R^4$ is alkyl of 1 to 12 carbon atoms, phenyl, halophenyl, nitrophenyl, benzyl or nitrobenzyl,
or a salt thereof with a physiologically compatible cation.

2. A compound in accordance with claim 1, wherein X is oxygen.

3. A compound in accordance with claim 2, wherein R is halogen; $R^2$ is hydrogen, nitro, cyano or $NHR^3$; and $R^3$ is hydrogen, alkyl of 1 to 12 carbon atoms, alkanoyl of 1 to 12 carbon atoms or aroyl of 7 to 14 carbon atoms.

4. A compound in accordance with claim 3, wherein $R^1$ is halogen.

5. A compound in accordance with claim 1, (±)-6-fluoro-8-acetamido-2,3-dihydrospiro[4H-1-benzopyran-4,5'-thiazolidine]-2',4'-dione.

6. A compound in accordance with claim 1, (±)methyl-6-fluoro-2,3-dihydro-2',4'-dioxospiro[4H-1-benzopyran-4,5'-thiazolidine]-8-carbamate.

7. A compound in accordance with claim 1, selected from the group consisting of:
(±)-6-Fluoro-2,3-dihydrospiro[4H-1-benzpyran-4,5'-thiazolidine]-2',4'-dione,
(±)-6-fluoro-8-nitro-2,3-dihydrospiro[4H-1-benzopyran-4,5'-thiazolidine]-2',4'-dione,
(±)-6-fluoro-8-amino-2,3-dihydrospiro[4H-1-benzopyran-4,5'-thiazolidine]-2',4'-dione,
6-fluoro-2,3-dihydrospiro[4H-1-benzopyran-4,5'-thiazolidine]-2',4'-dione and
(±)-6-fluoro-8-undecylamido-2,3-dihydrospiro[4H-1-benzopyran-4,5'-thiazolidine]-2',4'-dione.

8. A compound in accordance with claim 1, selected from the group consisting of:
(±)-6-Fluoro-8-hydroxy-2,3-dihydrospiro[4H-1-benzopyran-4,5'-thiazolidine]-2',4'-dione,
(±)-1-ethyl-3-[6-fluoro-2,3-dihydro-2',4'-dioxospiro[4H-1-benzopyran-4,5'-thiazolidine]-8-yl]urea,
(±)-8-cyano-6-fluoro-2,3-dihydrospiro[4H-1-benzopyran-4,5'-thiazolidine]-2',4'-dione,
(±)-ethyl-6-fluoro-2,3-dihydro-2',4'-dioxospiro[4H-1-benzopyran-4,5'-thiazolidine]-8-carbamate,
(±)-6-chloro-2,3-dihydrospiro[4H-1-benzopyran-4,5'-thiazolidine]-2',4'-dione,
(±)-N-[6-fluoro-2,3-dihydro-2',4'-dioxospiro[4H-1-benzopyran-4,5'-thiazolidin]-8-yl]formamide,
(±)-butyl-6-fluoro-2,3-dihydro-2',4'-dioxospiro[4H-1-benzopyran-4,5'-thiazolidine]-8-carbamate,
(±)-isobutyl-6-fluoro-2,3-dihydro-2',4'-dioxospiro[4H-1-benzopyran-4,5'-thiazolidine]-8-carbamate,
(±)-phenyl-6-fluoro-2,3-dihydro-2',4'-dioxospiro[4H-1-benzopyran-4,5'-thiazolidine]-8-carbamate,
(±)-benzyl-6-fluoro-2,3-dihydro-2',4'-dioxospiro[4H-1-benzopyran-4,5'-thiazolidine]-8-carbamate,
(±)-p-nitrophenyl-6-fluoro-2,3-dihydro-2',4'-dioxospiro[4H-1-benzopyran-4,5'-thiazolidine]-8-carbamate,
(±)-p-nitrobenzyl-6-fluoro-2,3-dihydro-2',4'-dioxospiro[4H-1-benzopyran-b 4,5'-thiazolidine]-8-carbamate,
(±)-p-(methoxycarbonyl)phenyl-6-fluoro-2,3-dihydro-2',4'-dioxospiro[4H-1-benzopyran-4,5'-thiazolidine]-8-carbamate,
(±)-N-[6-fluoro-2,3-dihydro-2',4'-dioxospiro[4H-1-benzopyran-4,5'-thiazolidin]-8-yl]pivalamide
(±)-N-[6-fluoro-2,3-dihydro-2',4'-dioxospiro[4H-1-benzopyran-4,5'-thiazolidin]-8-yl]-3,3-dimethylbutyramide,
(±)-N-[6-fluoro-2,3-dihydro-2',4'-dioxospiro[4H-1-benzopyran-4,5'-thiazolidin]-8-yl]benzamide,
(±)-p-bromo-N-2,3-dihydro-6-fluoro-2',4'-dioxospiro[4H-1-benzopyran-4,5'-thiazolidin-8'-yl]benzamide,
(±)-N-[6-fluoro-2,3-dihydro-2',4'-dioxospiro[4H-1-benzopyran-4,5'-thiazolidin]-8-yl]-p-nitrobenzamide,
(±)-N-[6-fluoro-2,3-dihydro-2',4'-dioxospiro[4H-1-benzopyran-4,5'-thiazolidin]-8-yl]-3,5-dinitrobenzamide, and
(±)-[[6fluoro-2,3-dihydro-2',4'-dioxospiro[4H-1-benzopyran-4,5'-thiazolidin]-8-yl]carbamoyl]methylacetate.

9. A method of treating diabetes mellitus which comprises administering an effective amount of a compound of the formula

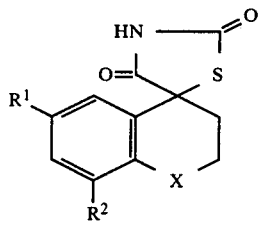

wherein

X is methylene, oxygen or sulfur; $R^1$ is halogen; $R^2$ is hydrogen, nitro, cyano, $OR^3$ or $NHR^3$; or $R^1$ and $R^2$ both simultaneously are hydrogen or nitro; $R^3$ is hydrogen, alkyl of 1 to 12 carbon atoms, alkanoyl of 1 to 12 carbon atoms, aroyl of 7 to 14 carbon atoms, —CO—$OR^4$ or —CO—$NHR^4$; and $R^4$ is alkyl of 1 to 12 carbon atoms, phenyl, halophenyl, nitrophenyl, benzyl or nitrobenzyl, or a salt thereof with a physiologically compatible cation.

10. A pharmaceutical composition for the treatment of diabetes mellitus comprising an effective amount of a compound of the formula

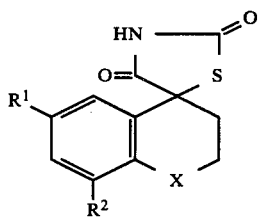

wherein

X is methylene, oxygen or sulfur; $R^1$ is halogen; $R^2$ is hydrogen, nitro, cyano, $OR^3$ or $NHR^3$; or $R^1$ and $R^2$ both simultaneously are hydrogen or nitro; $R^3$ is hydrogen, alkyl of 1 to 12 carbon atoms, alkanoyl of 1 to 12 carbon atoms, aroyl of 7 to 14 carbon atoms, —CO—$OR^4$ or —CO—$NHR^4$ is alkyl of 1 to 12 carbon atoms, phenyl, halophenyl, nitrophenyl, benzyl or nitrobenzyl, or a salt thereof with a physiologically compatible cation, and an inert pharmaceutical carrier.

11. A compound of the formula

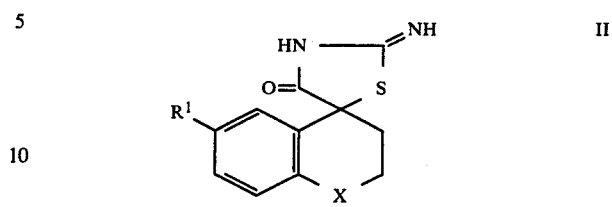

wherein $R^1$ is halogen and X is methylene, oxygen or sulfur.

12. A compound in accordance with claim 9, wherein X is oxygen.

13. A compound in accordance with claim 12, wherein $R^1$ is halogen, $R^2$ is hydrogen, nitro, cyano or $NHR^3$; and $R^3$ is hydrogen, alkyl of 1 to 12 carbon atoms, alkanoyl of 1 to 12 carbon atoms or aroyl of 7 to 14 carbon atoms.

14. A compound in accordance with claim 13, wherein $R^1$ is halogen.

15. A compound in accordance with claim 9, (±)-6-fluoro-8-acetamido-2,3-dihydrospiro[4H-1-benzopyran-4,5'-thiazolidine]-2',4'-dione.

16. A compound in accordance with claim 9, (±)methyl-6-fluoro-2,3-dihydro-2'-4'-dioxospiro[4H-1-benzopyran-4,5'-thiazolidine]-8-carbamate.

17. A compound in accordance with claim 10, wherein X is oxygen.

18. A compound in accordance with claim 17, wherein $R^1$ is halogen; $R^2$ is hydrogen, nitro, cyano or $NHR^3$; and $R^3$ is hydrogen, alkyl of 1 to 12 carbon atoms, alkanoyl of 1 to 12 carbon atoms or aroyl of 7 to 14 carbon atoms.

19. A compound in accordance with claim 18, wherein $R^1$ is halogen.

20. A compound in accordance with claim 10, (±)-6-fluoro-8-acetamido-b 2,3-dihydrospiro[4H-1-benzopyran-4,5'-thiazolidine]-2',4'-dione.

21. A compound in accordance with claim 10, (±)methyl-6-fluoro-2,3-dihydro-2'-4'-dioxospiro[4H-1-benzopyran-4,5'-thiazolidine]-8-carbamate.

22. A compound in accordance with claim 11, wherein X is oxygen.

* * * * *

UNITED STATES PATENT AND TRADEMARK OFFICE
CERTIFICATE OF CORRECTION

PATENT NO. : 4,587,256
DATED : May 6, 1986
INVENTOR(S) : HEINZ HASLER, FERNAND SCHNEIDER

It is certified that error appears in the above-identified patent and that said Letters Patent is hereby corrected as shown below:

In claim 7, line 67, delete "benzpyran" and insert --benzopyran--.

In claim 8, line 40, delete "benzopyran-b  4,5'" and insert --benzopyran-4,5'--.

Signed and Sealed this

Twelfth Day of July, 1988

Attest:

DONALD J. QUIGG

Attesting Officer

Commissioner of Patents and Trademarks